United States Patent [19]

Böger et al.

[11] 4,115,583
[45] Sep. 19, 1978

[54] PESTICIDAL SULPHENYLATED FORMAMIDINE COMPOUNDS

[75] Inventors: Manfred Böger, Weil am Rhein, Germany; Jozef Drabek, Allschwil, Switzerland

[73] Assignee: Ciba-Geigy Corporation, Ardsley, N.Y.

[21] Appl. No.: 792,754

[22] Filed: May 2, 1977

Related U.S. Application Data

[62] Division of Ser. No. 646,814, Jan. 6, 1976, abandoned.

[30] Foreign Application Priority Data

Jan. 16, 1975 [CH] Switzerland ............................ 534/75
Jun. 26, 1975 [CH] Switzerland ........................... 8310/75
Nov. 7, 1975 [CH] Switzerland ......................... 14425/75

[51] Int. Cl.$^2$ ...................... C07C 145/04; A01N 9/12
[52] U.S. Cl. .............................. 424/300; 260/465 D; 260/557 R; 260/562 R; 424/304; 424/324; 560/16
[58] Field of Search .......................... 560/16; 424/300; 260/465 D

[56] References Cited

U.S. PATENT DOCUMENTS

| | | | |
|---|---|---|---|
| 3,766,243 | 10/1973 | Widdig | 260/470 |
| 3,835,184 | 9/1974 | Ost | 424/324 |
| 3,903,162 | 9/1975 | Chupp | 260/562 B |
| 3,947,591 | 3/1976 | Rizzo | 260/551 S |
| 3,960,947 | 6/1976 | Duerr | 260/562 R |

Primary Examiner—Bernard Helfin
Assistant Examiner—Michael Shippen
Attorney, Agent, or Firm—Frederick H. Rabin

[57] ABSTRACT

Compounds of the formula I

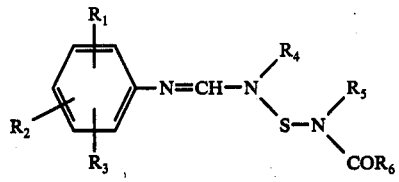

wherein $R_1$, $R_2$ and $R_3$ independently of one another represent hydrogen, halogen, $C_1$-$C_4$-alkyl, $C_1$-$C_4$-alkoxy, $C_1$-$C_4$-alkylthio, trifluoromethyl, cyano or nitro, $R_4$ represents $C_1$-$C_4$-alkyl, $R_5$ represents an optionally halogen substituted $C_1$-$C_{10}$-alkyl; or $C_3$-$C_{10}$-cycloalkyl, $C_4$-$C_{10}$-(cycloalkylalkyl) or $C_2$-$C_{10}$-(alkoxyalkyl) and $R_6$ represents hydrogen; optionally halogen substituted $C_1$-$C_{10}$-alkyl or $C_1$-$C_{10}$-alkoxy; or $C_2$-$C_{10}$-cycloalkyl, $C_3$-$C_{10}$-cycloalkoxy, $C_4$-$C_{10}$-(cycloalkylalkyl), $C_4$-$C_{10}$-(cycloalkylalkoxy), $C_2$-$C_{10}$-(alkoxyalkyl) or $C_2$-$C_{10}$-(alkoxyalkoxy)

are valuable pesticidal, in particular insecticidal and acaricidal, agents.

20 Claims, No Drawings

PESTICIDAL SULPHENYLATED FORMAMIDINE COMPOUNDS

This is a division of application Ser. No. 646,814, filed on Jan. 6, 1976 now abandoned.

BRIEF SUMMARY OF THE INVENTION

The present invention relates to new sulphenylated phenylformamidines which have a pesticidal action, to processes for producing them, as well as to pest-control agents containing these formamidines as active ingredients, and to processes for combatting pests by application of the new formamidines.

DETAILED DISCLOSURE

The new phenylformamidines of the invention correspond to the formula I

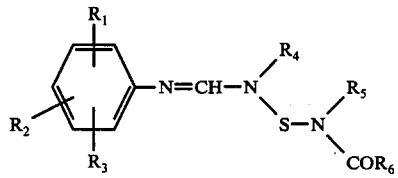

wherein
$R_1$, $R_2$ and $R_3$ each independently represent a hydrogen or halogen atom or a $C_1$-$C_4$-alkyl, $C_1$-$C_4$-alkoxy, $C_1$-$C_4$-alkylthio, trifluoromethyl, cyano or nitro group,
$R_4$ represents a $C_1$-$C_4$-alkyl group,
$R_5$ represents an optionally halogen-substituted $C_1$-$C_{10}$-alkyl group or a $C_3$-$C_{10}$-cycloalkyl, $C_4$-$C_{10}$-(cycloalkylalkyl) or $C_2$-$C_{10}$-(alkoxyalkyl) group, and
$R_6$ represents a hydrogen atom; an optionally halogen-substituted $C_1$-$C_{10}$-alkyl or $C_1$-$C_{10}$-alkoxy group; or a $C_3$-$C_{10}$-cycloalkyl, $C_3$-$C_{10}$-cycloalkyloxy, $C_4$-$C_{10}$-(cycloalkylalkyl), $C_4$-$C_{10}$-(cycloalkylalkoxy), $C_2$-$C_{10}$-(alkoxyalkyl) or $C_2$-$C_{10}$-(alkoxyalkoxy) group.

Of special importance on account of their action against pests, especially against insects and, in particular, against members of the order Acarina, are compounds of the above-mentioned formula I wherein
$R_1$ represents a $C_1$-$C_4$-alkyl group (particularly a methyl group) in the ortho-position,
$R_2$ represents a $C_1$-$C_4$-alkyl group (particularly a methyl group) or a halogen atom (especially a chlorine or bromine atom) in the para-position,
$R_3$ represents a hydrogen atom, and
$R_4$ represents a methyl group, while
$R_5$ and $R_6$ have the meanings already defined under formula I;
and particularly preferred compounds of the formula I are those wherein
$R_1$ represents a $C_1$-$C_4$-alkyl group (especially a methyl group) in the ortho-position,
$R_2$ represents a $C_1$-$C_4$-alkyl group (especially a methyl group) or a halogen atom (particularly a chlorine or bromine atom) in the para-position,
$R_3$ represents a hydrogen atom, and
$R_4$ represents a methyl group, and either
i. $R_5$ represents an optionally halogen-substituted $C_1$-$C_{10}$-alkyl group or a $C_3$-$C_{10}$-cycloalkyl, $C_4$-$C_{10}$-(cycloalkylalkyl) or $C_2$-$C_{10}$-(alkoxyalkyl) group, especially a $C_1$-$C_{10}$-alkyl, $C_3$-$C_6$-cycloalkyl, $C_3$-$C_6$-cycloalkyl-$C_1$-$C_2$-alkyl or $C_1$-$C_4$-alkoxy-$C_1$-$C_4$-alkyl group, while
$R_6$ stands for a hydrogen atom; or
ii. $R_5$ represents an optionally halogen-substituted $C_1$-$C_{10}$-alkyl group, particularly an optionally halogen-substituted $C_1$-$C_4$-alkyl group, while
$R_6$ stands for an optionally halogen-substituted $C_1$-$C_{10}$-alkyl or $C_1$-$C_{10}$-alkoxy group or a $C_3$-$C_{10}$-cycloalkyl, $C_3$-$C_{10}$-cycloalkoxy, $C_4$-$C_{10}$-(cycloalkylalkyl), $C_4$-$C_{10}$-(cycloalkylalkoxy), $C_2$-$C_{10}$-(alkoxyalkyl) or $C_2$-$C_{10}$-(alkoxyalkoxy) group, particularly a $C_1$-$C_{10}$-alkyl, $C_1$-$C_{10}$-alkoxy, $C_3$-$C_6$-cycloalkyl-$C_1$-$C_2$-alkyl, $C_3$-$C_6$-cycloalkyl-$C_1$-$C_2$-alkoxy, $C_1$-$C_4$-alkoxy-$C_1$-$C_4$-alkyl or $C_1$-$C_4$-alkoxy-$C_1$-$C_4$-alkoxy group.

Alkyl groups in the formula I can be branched-chain or straight chain; and examples of such groups are the methyl, ethyl, n-propyl, isopropyl, n-butyl, isobutyl, sec.-butyl and tert.-butyl group, and for $R_5$ and $R_6$ also the n-pentyl, n-hexyl, n-heptyl, n-octyl, n-nonyl and n-decyl group and isomers thereof. Such alkyl groups form also the alkyl moieties of alkoxy, alkylthio, alkoxyalkyl and alkoxyalkoxy substituents. Furthermore, alkyl groups and alkoxy groups denoted by $R_5$ and $R_6$ can be substituted by one or more halogen atoms, especially by 1 to 4 chlorine and/or bromine atoms.

By "cycloalkyl groups" are meant the cyclopropyl, cyclobutyl, cyclopentyl, cyclohexyl, cycloheptyl, cyclooctyl, cyclononyl and cyclodecyl group, particularly the cyclopropyl, cyclohexyl and cyclooctyl group. These groups form also the cycloalkyl moiety of cycloalkylalkyl and cycloalkylalkoxy groups, such as the cyclopropylmethyl, 2-cyclopropylethyl, cyclohexylmethyl, cyclooctylmethyl, 4-cyclopropyl-n-butyl, 4-cyclopropyl-3-methyl-n-butyl, cyclopropylmethoxy, cyclohexylmethoxy and cyclooctylmethoxy group.

By halogen atoms are meant the fluorine, chlorine, bromine and iodine atoms, especially the chlorine or bromine atom.

The new sulphenylated phenylformamidines of the formula I are obtained by methods known per se; they are obtained, for example, by reacting a compound of the formula II

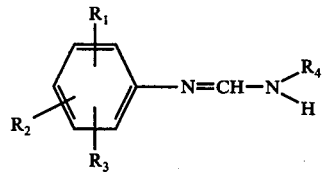

in the presence of a base, with a compound of the formula III

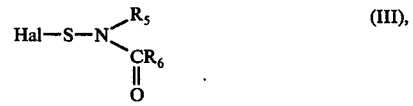

with $R_1$ to $R_6$ in the formulae II and III having the meanings already defined under formula I, and "Hal" standing for a halogen atom, particularly a chlorine or bromine atom.

The process is performed at a reaction temperature of between −20° and 30° C., at normal or elevated pressure and preferably in a solvent or diluent inert to the reactants. Suitable solvents or diluents for this reaction are, e.g., ethers and ethereal compounds, such as diethyl ether, di-isopropyl ether, dioxane, dimethoxyethane and tetrahydrofuran; amides such as N,N-di-alkylated carboxylic acid amides; aliphatic and aromatic as well as halogenated hydrocarbons, particularly benzene, toluene, xylenes, chloroform and chlorobenzene; nitriles such as acetonitriles; dimethylsulphoxide and ketones such as acetone and methyl ethyl ketone.

Suitable bases are, in particular, tertiary amines such as triethylamine, dimethylaniline, pyridine, picolines and lutidines, also hydroxides, oxides, carbonates and bicarbonates of alkali metals and alkaline-earth metals, as well as alkali metal alcoholates such as potassium-t.butylate and sodium methylate.

The derivatives of the formulae II and III used as starting materials are known and can be produced by methods known per se.

The compounds of the formula I have a broad biocidal action and can be used to combat various plant and animal pests; they can be used, e.g., as acaricides, insecticides, ectoparasiticides and also as plant-growth regulators or as herbicides.

They are suitable, in particular, for combatting acarids, e.g. of the families: Ixodidae, Argasidae, Tetranychidae and Dermanysidae; it is also to be mentioned in this connection that compounds of the formula I wherein $R_1$ represents o-methyl, $R_2$ p-chlorine and $R_3$ hydrogen have an excellent long term action on larvae and adults, while such compounds wherein $R_1$ represents o-methyl, $R_2$ p-methyl and $R_3$ hydrogen are primarily effective as ovicides.

Furthermore, the compounds of the formula I have a favourable effect against insects injurious to plants and to animals, and can be used, for combatting, for example, insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae; and, in particular, for combatting aphids (e.g. Myzus persicae). The compounds of the formula I are therefore particularly suitable for the control of phytopathogenic insects in crops of fruit, vegetables and ornamental plants.

The acaricidal or insecticidal action can be appreciably broadened and adapted to suit given circumstances by the addition of other insecticides and/or acaricides. Suitable additives are, e.g.: organic phosphorus compounds, nitrophenols and derivatives thereof, formamidines, ureas, pyrethrin-like compounds, carbamates and chlorinated hydrocarbons.

The compounds of the formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers.

For application, the compounds of the formula I can be processed into the form of dusts, emulsion concentrates, granulates, dispersions, sprays of solutions, the formulation of these preparations being effected in a manner commonly known in practice.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations:
  dusts, scattering agents, granulates (coated granulates, impregnated granulates and homogeneous granulates);
liquid preparations:
  a. water-dispersible active-substance concentrates: wettable powders, pastes or emulsions;
  b. solutions.

The content of active substance in the described compositions is between 0.1 and 95%, in this connection it is to be mentioned that in the case of application from an aeroplane, or by means of other suitable devices, even higher concentrations may be used.

The active substances of the formula I can be formulated, for example, as follows:

Dusts:
The following substances are used in the preparation of a) a 5% dust, and b) a 2% dust:
a.
  5 parts of active substance,
  95 parts of talcum;
b.
  2 parts of active substance,
  1 part of highly dispersed silicic acid,
  97 parts of talcum.

The active substances are mixed and ground with the carriers.

Granulate:
The following substances are used to produce a 5% granulate:
  5 parts of active substance,
  0.25 part of epichlorohydrin,
  0.25 part of cetyl polyglycol ether,
  3.50 parts of polyethylene glycol,
  91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder:
The following constituents are used to prepare a) a 40%, b) and c) a 25%, and d) a 10% wettable powder:
a.
  40 parts of active substance,
  5 parts of sodium lignin sulphonate,
  1 part of sodium dibutyl-naphthalene sulphonate,
  54 parts of silicic acid;
b.
  25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin;
c.
  25 parts of active substance,
  2.5 parts of isooctylphenoxy-polyoxyethyleneethanol,
  1.7 parts of Champagne chalk/hydroxyethyl cellulose mixture (1:1), 8.3 parts of sodium aluminium silicate,
16.5 parts of kieselguhr,
46 parts of kaolin;

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in the appropriate mills and rollers. Wettable powders are obtained which can be diluted with water to give suspensions of any desired concentration.

Emulsifiable concentrates:

The following substances are used to produce a) a 10%, b) a 25%, and c) a 50% emulsifiable concentrate:

a.
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

b.
25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;

c.
50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration.

Spray:

The following constituents are used to prepare a) a 5% spray, and b) a 95% spray:

a.
5 parts of active substance,
1 part of epichlorohydrin,
94 parts of ligroin (boiling limits 160°–190° C.);

b.
95 parts of active substance,
5 parts of epichlorohydrin.

The invention is further illustrated by the following Examples.

EXAMPLE 1

A. Production of 1,3,5-triaza-4-sulpha-1-(2-methyl-4-chlorophenyl)-3-methyl-5-acetyl-hexene-(1)

14.0 g of N-methyl-acetamidosulphenyl chloride is slowly added dropwise at 0° to 10° C., with continuous stirring, to a solution of 18.2 g of N-methyl-N'-(4-chloro-2-methylphenyl)-formamidine in 60 ml of pyridine. The mixture is stirred for a further 20 minutes at this temperature; the unreacted pyridine is then removed at 1 mm Hg pressure at 50° C. To the semicrystalline residue there are subsequently added 150 ml of toluene and 100 ml of ice-water; the toluene phase is washed three times with 80 ml of ice-water each time, dried over sodium sulphate, concentrated by evaporation and finally dried in high vacuum at 40° C.

There is obtained the compound of the formula

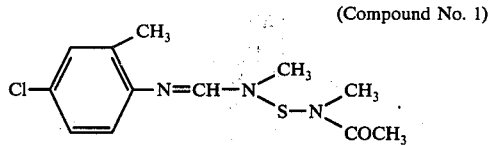

(Compound No. 1)

in the form of yellow oil having a refractive index of $n_D^{20}$:1.5933.

B. Production of 1,3,5-triaza-4-sulpha-1-(2-methyl-4-chlorophenyl)-3-methyl-5-formyl-7-methoxy-heptene-(1)

10.2 g of triethylamine is added to a solution of 18.2 g of N-methyl-N'-(4-chloro-2-methylphenyl)-formamidine in 200 ml of tetrahydrofuran. There is then slowly added dropwise at 5° to 15° C., with continuous stirring, 17.0 g of N-formyl-methoxyethylaminesulphenyl chloride; stirring is afterwards continued for 30 minutes at room temperature, the triethylamine hydrochloride is filtered off, the filtrate is concentrated by evaporation and the residue is finally dried in high vacuum.

There is obtained the compound of the formula

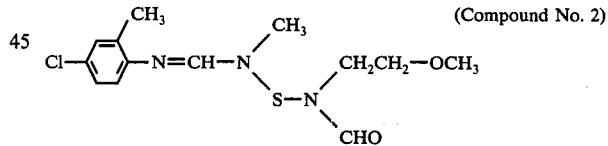

(Compound No. 2)

in the form of a yellow oil having a refractive index of $n_D^{20} = 1.5781$.

C. The following compounds of the formula Ia, Ib or Ic are produced in an analogous manner:

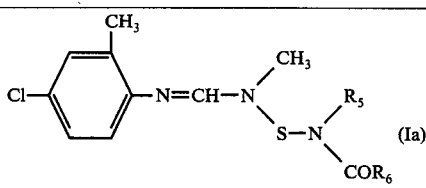

(Ia)

| Compound No. | $R_5$ | $R_6$ | Physical data |
|---|---|---|---|
| 3 | $CH_3-$ | H | $n_D^{20}$: 1,6008 |
| 4 | $C_2H_5-$ | H | $n_D^{20}$: 1,5880 |
| 5 | $(n)C_3H_7-$ | H | |
| 6 | $(i)C_3H_7-$ | H | $n_D^{20}$ 1,5815 |
| 7 | $(i)C_4H_9-$ | H | |

-continued

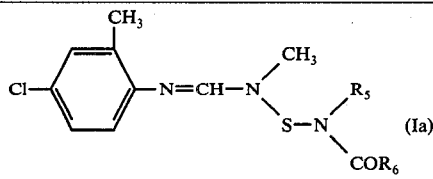

| Compound No. | $R_5$ | $R_6$ | Physical data |
|---|---|---|---|
| 8 | $CH_3-$ | $CH_3O-$ | $n_D^{20}: 1,5780$ |
| 9 | $C_2H_5-$ | $CH_3O-$ | $n_D^{20}: 1,5552$ |
| 10 | $(n)C_4H_9-$ | $CH_3O-$ | $n_D^{20}: 1,5739$ |
| 11 | $ClCH_2CH_2-$ | $CH_3O-$ | $n_D^{20}: 1,5635$ |
| 12 | $CH_3-$ | $C_2H_5O-$ | $n_D^{20}: 1,5550$ |
| 13 | $CH_3-$ | $(n)C_4H_9O-$ | $n_D^{20}: 1,5536$ |
| 14 | $CH_3-$ | $(i)C_4H_9O-$ | $n_D^{20}: 1,5561$ |
| 15 | $CH_3-$ | $(sec.)C_4H_9O-$ | $n_D^{20}: 1,5406$ |
| 16 | $(n)C_4H_9-$ | $(n)C_4H_9O-$ | $n_D^{20}: 1,5531$ |
| 17 | $CH_3(CH_2)_3CH-CH_2- \atop C_2H_5$ | H | |
| 18 | ▷$-CH_2-$ | H | $n_D^{20}: 1,5875$ |
| 19 | $CH_3-$ | $CH_3OCH_2CH_2O-$ | m.p.: 57–59° C |
| 20 | $CH_3-$ | $(n)C_8H_{17}O-$ | $n_D^{20}: 1,5386$ |
| 21 | $CH_3-$ | $(n)C_{10}H_{21}O-$ | $n_D^{20}: 1,5350$ |
| 22 | $CH_3-$ | ⬡H$-O-$ | $n_D^{20}: 1,5658$ |
| 23 | $CH_3-$ | ▷ | $n_D^{20}: 1,5925$ |
| 24 | ▷ | H | m.p.: 44–47° C |
| 25 | $CH_3-$ | $(n)C_6H_{13}O-$ | $n_D^{20}: 1,5480$ |
| 26 | ⬡H$-$ | H | $n_D^{20}: 1,5849$ |

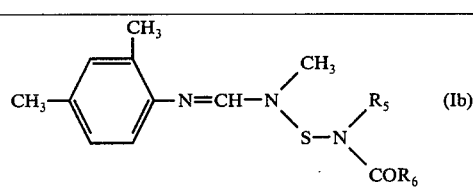

| Compound No. | $R_5$ | $R_6$ | Physical data |
|---|---|---|---|
| 27 | $CH_3-$ | H | $n_D^{20}: 1,5879$ |
| 28 | $C_2H_5-$ | H | $n_D^{20}: 1,5764$ |
| 29 | $(n)C_3H_7-$ | H | $n_D^{20}: 1,5653$ |
| 30 | $(i)C_3H_7-$ | H | $n_D^{20}: 1,5679$ |
| 31 | $(i)C_4H_9-$ | H | $n_D^{20}: 1,5539$ |
| 32 | $CH_3-$ | $CH_3-$ | $n_D^{20}: 1,5800$ |
| 33 | $CH_3-$ | $CH_3O-$ | $n_D^{20}: 1,5639$ |
| 34 | $C_2H_5-$ | $CH_3O-$ | $n_D^{20}: 1,5559$ |
| 35 | $(n)C_4H_9-$ | $CH_3O-$ | $n_D^{20}: 1,5460$ |
| 36 | $ClCH_2CH_2-$ | $CH_3O-$ | $n_D^{20}: 1,5644$ |
| 37 | $CH_3-$ | $C_2H_5O-$ | $n_D^{20}: 1,5537$ |
| 38 | $CH_3-$ | $(n)C_4H_9O-$ | $n_D^{20}: 1,5420$ |
| 39 | $CH_3-$ | $(i)C_4H_9O-$ | $n_D^{20}: 1,5414$ |
| 40 | $CH_3-$ | $(sec.)C_4H_9O-$ | $n_D^{20}: 1,5451$ |
| 41 | $(n)C_4H_9-$ | $(n)C_4H_9O-$ | $n_D^{20}: 1,5270$ |
| 42 | $CH_3OCH_2CH_2-$ | H | $n_D^{20}: 1,5640$ |
| 43 | $CH_3(CH_2)_3CH-CH_2- \atop C_2H_5$ | H | $n_D^{20}: 1,5415$ |
| 44 | ▷$-CH_2-$ | H | $n_D^{20}: 1,5728$ |

-continued

| Compound No. | $R_5$ | $R_6$ | Physical data |
|---|---|---|---|
| 45 | $CH_3-$ | $CH_3OCH_2CH_2O-$ | $n_D^{20}: 1,5509$ |
| 46 | $CH_3-$ | $(n)C_8H_{17}O-$ | $n_D^{20}: 1,5270$ |
| 47 | $CH_3-$ | $(n)C_{10}H_{21}O-$ | $n_D^{20}: 1,5263$ |
| 48 | $CH_3-$ | ⬡H$-O-$ | $n_D^{20}: 1,5522$ |
| 49 | $CH_3-$ | ▷ | $n_D^{20}: 1,5776$ |
| 50 | ▷ | H | $n_D^{20}: 1,5809$ |
| 51 | $CH_3-$ | $(n)C_6H_{13}O-$ | $n_D^{20}: 1,5362$ |
| 52 | ⬡H$-$ | H | $n_D^{20}: 1,5749$ |

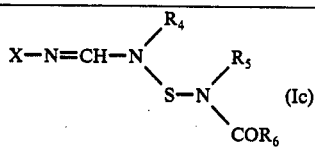

$$X-N=CH-N\diagdown^{R_4}_{S-N\diagdown^{R_5}_{COR_6}} \qquad (Ic)$$

| Comp. No. | X | $R_4$ | $R_5$ | $R_6$ | Physical data |
|---|---|---|---|---|---|
| 53 | 2-CH₃-4-Br-phenyl- | CH₃— | C₂H₅— | H | $n_D^{20}$: 1,6042 |
| 54 | 2-CH₃-4-Br-phenyl- | CH₃— | CH₃— | CH₃— | $n_D^{20}$: 1,6073 |
| 55 | 2-CH₃-4-Br-phenyl- | CH₃— | C₂H₅— | CH₃O— | $n_D^{20}$: 1,5811 |
| 56 | 2-CH₃-4-Br-phenyl- | CH₃— | CH₃— | C₂H₅O— | $n_D^{20}$: 1,5804 |
| 57 | 2,5-di-CH₃-4-Br-phenyl- | CH₃— | CH₃— | H | $n_D^{20}$: 1,6130 |
| 58 | 2-CH₃-3-Cl-phenyl- | CH₃— | CH₃— | H | |
| 59 | 2-CH₃-6-Cl-phenyl- | CH₃— | CH₃— | C₄H₉O— | $n_D^{20}$: 2,5449 |
| 60 | 2-CH₃-4-Cl-phenyl- | C₄H₉— | CH₃— | H | $n_D^{20}$: 1,5780 |
| 61 | 3,5-bis-CF₃-phenyl- | CH₃— | CH₃— | H | m.p.: 50–51° C |
| 62 | 4-NO₂-phenyl- | CH₃— | CH₃— | H | m.p.: 85–87° C |
| 63 | 2,3-di-Cl-phenyl- | CH₃— | CH₃— | H | m.p.: 87–90° C |
| 64 | 2,3-di-Cl-phenyl- | CH₃— | CH₃— | CH₃O— | $n_D^{20}$: 1,5841 |
| 65 | 2,4,5-tri-Cl-phenyl- | CH₃— | CH₃— | H | m.p.: 103–104° C |
| 66 | 2,4,5-tri-Cl-phenyl- | CH₃— | CH₃— | CH₃O— | m.p.: 68–72° C |
| 67 | 2,4,5-tri-Cl-phenyl- | CH₃— | ClCH₂CH₂— | CH₃O— | $n_D^{20}$: 1,5915 |
| 68 | 2,4,5-tri-Cl-phenyl- | CH₃— | CH₃— | C₂H₅O— | m.p.: 55–57° C |
| 69 | 2,4,5-tri-Cl-phenyl- | CH₃— | CH₃— | (i)C₄H₉O— | $n_D^{20}$: 1,5738 |
| 70 | 2,4-Cl-phenyl- | CH₃— | CH₃— | H | $n_D^{20}$: 1,6143 |
| 71 | 2,6-di-Cl-phenyl- | CH₃— | CH₃— | H | |
| 72 | 2,6-di-Cl-phenyl- | CH₃— | CH₃— | CH₃O— | $n_D^{20}$: 1,5809 |
| 73 | 2-Cl-phenyl- | CH₃— | CH₃— | H | $n_D^{20}$: 1,6135 |
| 74 | 3,5-di-Cl-phenyl- | CH₃— | CH₃— | H | $n_D^{20}$: 1,6183 |
| 75 | 3,5-di-Cl-phenyl- | CH₃— | CH₃— | CH₃O— | $n_D^{20}$: 1,5923 |
| 76 | 3,5-di-Cl-phenyl- | CH₃— | CH₃— | (n)C₄H₉O— | $n_D^{20}$: 1,5655 |
| 77 | 3,5-di-Cl-phenyl- | CH₃— | CH₃— | (i)C₄H₉O— | $n_D^{20}$: 1,5653 |
| 78 | 2,6-di-C₂H₅-phenyl- | CH₃— | ClCH₂CH₂— | CH₃O— | $n_D^{20}$: 1,5492 |
| 79 | 2,6-di-C₂H₅-phenyl- | CH₃— | (n)C₄H₉— | CH₃O— | $n_D^{20}$: 1,5309 |
| 80 | 2-CH₃-4-Br-phenyl- | CH₃— | CH₃OCH₂CH₂— | H | $n_D^{20}$: 1,5934 |
| 81 | 3,5-bis-CF₃-phenyl- | CH₃— | ▷—CH₂— | H | $n_D^{20}$: 1,5083 |
| 82 | 3,5-di-Cl-phenyl- | CH₃— | CH₃OCH₂CH₂— | H | $n_D^{20}$: 1,5934 |
| 83 | 2,4,5-tri-Cl-phenyl- | CH₃— | CH₃— | ⟨H⟩—O— | m.p.: 57–61° C |
| 84 | 4-NO₂-phenyl- | CH₃— | ▷ | H | m.p.: 67–70° C |

EXAMPLE 2

Acaricidal action

Phaseolus vulgaris (plants) were infested, 12 hours before the test for acaricidal action, with an infested piece of leaf from a mass culture of Tetranychus urticae. The transferred mobile stages were sprayed with the emulsified test preparations, at a concentration of 400 ppm, from a chromatography-sprayer in a manner ensuring no running-off of the spray liquor. An evaluation was made after 2 and 7 days, by examination under a binocular, of the living and of the dead larvae, adults and eggs. The treated plants were kept during the "holding time" in greenhouse compartments at 25° C.

The compounds according to the Example 1 were effective in the above test against adults, larvae and eggs of Tetranychus urticae. Compounds to be given special mention on account of their particularly good action are Compounds 1–23, 25, 28, 30, 33, 35, 36, 37–44, 46–49, 51 and 56.

EXAMPLE 3

Action on ticks

A. Rhipicephalus bursa

For each concentration, 5 adult ticks and 50 tick larvae were placed into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks, and in the case of the larvae after 2 days. There were two repeats for each test.

B. Boophilus microplus (larvae)

With a dilution series analogous to that in Test A, tests were carried out with 20 sensitive larvae and OP-resistant larvae, respectively (resistance is with respect to diazinon compatibility).

The compounds according to Example 1 were effective in these tests against adults and larvae of Rhipicephalus bursa and against sensitive and OP-resistant larvae, respectively, of Boophilus microplus.

EXAMPLE 4

Broad beans (Vicia faba) grown in pots were infested with the test insects (Myzus persicae), the average infestation being about 200 insects per plant.

The test substance (0.1% aqueous emulsion obtained from a 10% emulsifiable concentrate) was applied, 24 hours after infestation, by means of a compressed-air sprayer, the sprayed jet being directed from a distance of 30 cm onto the leaves infested with bean aphids.

Two plants were used per test substance. The test was carried out at a temperature of 24° C. with 60% relative humidity.

Compounds, 2, 6, 10, 12, 13, 15, 17–19, 25, 33–35, 37, 38, 40, 42–45, 50–52, 59 and 79 according to Example 1 exhibited in the above test a good effect against Myzus persicae.

EXAMPLE 5

Seeds of the grasses Lolium perenne, Zoa pratensis, Festuca ovina and Dactylis glomerata were sown in plastics dishes containing a soil/peat/sand mixture. After three weeks, the emerged grasses were cut back to a height of 4 cm above the soil, and 2 days later were sprayed with an aqueous spray liquor of the active substance. The amount of active substance was equivalent to 5 kg of active substance per hectare. The growth of the grasses was evaluated 14 days after application of the test liquor.

Compounds of the formula I exhibited in the above test a good inhibitory action on the growth of the grasses.

We claim:

1. A compound of the formula I

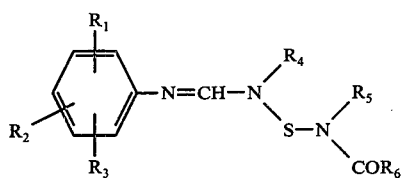

wherein
$R_1$, $R_2$ and $R_3$ independently of one another represent hydrogen, halogen, $C_1$–$C_4$-alkyl, $C_1$–$C_4$-alkoxy, $C_1$–$C_4$-alkylthio, trifluoromethyl, cyano or nitro,
$R_4$ represents $C_1$–$C_4$-alkyl,
$R_5$ represents an $C_1$–$C_{10}$-alkyl, halogen substituted $C_1$–$C_{10}$-alkyl; $C_3$–$C_{10}$-cycloalkyl, $C_4$–$C_{10}$-(cycloalkylalkyl) or $C_2$–$C_{10}$-(alkoxyalkyl) and
$R_6$ represents $C_1$–$C_{10}$-alkoxy; $C_3$–$C_{10}$-cycloalkoxy, $C_4$–$C_{10}$-(cycloalkylalkoxy) or $C_2$–$C_{10}$-(alkoxyalkoxy).

2. A compound according to claim 1 wherein
$R_1$ represents $C_1$–$C_4$-alkyl in the ortho-position,
$R_2$ represents $C_1$–$C_4$-alkyl or halogen in the para-position,
$R_3$ represents hydrogen and
$R_4$ represents methyl.

3. A compound according to claim 2 wherein
$R_1$ represents methyl in the ortho-position and
$R_2$ represents methyl, chlorine or bromine in the para-position.

4. A compound according to claim 1 wherein
$R_1$ represents $C_1$–$C_4$-alkyl in the ortho-position,
$R_2$ represents $C_1$–$C_4$-alkyl or halogen in the para-position,
$R_3$ represents hydrogen,
$R_4$ represents methyl,
$R_5$ represents $C_1$–$C_{10}$-alkyl or halogen substituted $C_1$–$C_{10}$-alkyl, and
$R_6$ represents $C_1$–$C_{10}$-alkoxy; or $C_3$–$C_{10}$-cycloalkoxy, $C_4$–$C_{10}$-(cycloalkylalkoxy), or $C_2$–$C_{10}$-(alkoxyalkoxy).

5. A compound according to claim 4 wherein
$R_1$ represents methyl in the ortho-position,
$R_2$ represents methyl, chlorine or bromine in the para-position
$R_5$ represents $C_1$–$C_4$-alkyl or halogen substituted $C_1$–$C_4$-alkyl and
$R_6$ represents, $C_1$–$C_{10}$-alkoxy, $C_3$–$C_6$-cycloalkoxy, $C_3$–$C_6$-cycloalkyl-$C_1$–$C_2$-alkoxy, or $C_1$–$C_4$-alkoxy-$C_1$–$C_4$-alkoxy.

6. 1,3,5-Triaza-4-sulfa-1-(2,4-dimethylphenyl)-3-methyl-5-methoxycarbonyl-nonene-(1), according to claim 5.

7. 1,3,5-Triaza-4-sulfa-1-(2,4-dimethylphenyl)-3-methyl-5-isobutoxycarbonyl-hexene-(1), according to claim 5.

8. 1,3,5-Triaza-4-sulfa-1-(2,4-dimethylphenyl)-3-methyl-5-sec.butoxycarbonyl-hexene-(1), according to claim 5.

9. 1,3,5-Triaza-4-sulfa-1-(2,4-dimethylphenyl)-3-methyl-5-cyclohexyloxycarbonyl-hexene-(1), according to claim 5.

10. 1,3,5-Triaza-4-sulfa-1-(2,4-dimethylphenyl)-3-methyl-5-n-hexyloxycarbonyl-hexene-(1), according to claim 5.

11. An insecticidal or acaricidal composition comprising an insecticidally or acaricidally effective amount of a compound according to claim 1 together with a solid or liquid diluent or carrier therefor.

12. A method of combatting pests of the class Insecta or of the order Acarina at a locus, which method comprises applying to the locus an insectidally or acaricidally effective amount of a compound as claimed in claim 1.

13. A method according to claim 12 wherein the locus comprises agricultural or horticultural crops or plants or stored goods of organic material.

14. A method according to claim 12 wherein the locus comprises commercially reared livestock or the environment thereof.

15. A method according to claim 12 wherein
$R_1$ represents methyl in the ortho position,
$R_2$ represents methyl, chlorine or bromine in the para position,
$R_3$ represents hydrogen,
$R_4$ represents methyl,
$R_5$ represents $C_1$–$C_4$-alkyl or halogen substituted $C_1$–$C_4$-alkyl, and
$R_6$ represents $C_1$–$C_{10}$-alkoxy, $C_3$–$C_6$-cycloalkoxy, $C_3$–$C_6$-cycloalkyl; $C_1$–$C_2$-alkoxy, or $C_1$–$C_4$-alkoxy-$C_1$–$C_4$-alkoxy.

16. The method according to claim 15 in which the compound is 1,3,5-triaza-4-sulfa-1-(2,4-dimethylphenyl)-3-methyl-5-methoxycarbonyl-nonene-(1).

17. The method according to claim 15 in which the compound is 1,3,5-triaza-4-sulfa-1-(2,4-dimethylphenyl)-3-methyl-5-isobutoxycarbonyl-hexene-(1).

18. The method according to claim 15 in which the compound is 1,3,5-triaza-4-sulfa-1-(2,4-dimethylphenyl)-3-methyl-5-sec.butoxycarbonyl-hexene-(1).

19. The method according to claim 15 in which the compound is 1,3,5-triaza-4-sulfa-1-(2,4-dimethylphenyl)-3-methyl-5-cyclohexyloxycarbonyl-hexene-(1).

20. The method according to claim 15 in which the compound is 1,3,5-triaza-4-sulfa-1-(2,4-dimethylphenyl)-3-methyl-5-n-hexyloxycarbonyl-hexene-(1).

* * * * *